(12) United States Patent
Barten et al.

(10) Patent No.: US 11,317,984 B2
(45) Date of Patent: May 3, 2022

(54) PROTECTIVE COVER FOR A PART OF A MEDICAL DEVICE

(71) Applicant: Drägerwerk AG & Co. KGaA, Lübeck (DE)

(72) Inventors: Ronny Barten, Lübeck (DE); Christian Hilleke, Lübeck (DE); Gerd Wotha, Warnsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 244 days.

(21) Appl. No.: 16/349,010

(22) PCT Filed: Nov. 8, 2017

(86) PCT No.: PCT/EP2017/001296
§ 371 (c)(1),
(2) Date: May 10, 2019

(87) PCT Pub. No.: WO2018/086736
PCT Pub. Date: May 17, 2018

(65) Prior Publication Data
US 2019/0262091 A1    Aug. 29, 2019

(30) Foreign Application Priority Data

Nov. 11, 2016   (DE) .................... 10 2016 013 394.5

(51) Int. Cl.
*A61B 46/10*   (2016.01)
*A61B 46/00*   (2016.01)
*A61B 90/30*   (2016.01)
*A61B 90/00*   (2016.01)

(52) U.S. Cl.
CPC .............. *A61B 46/10* (2016.02); *A61B 46/00* (2016.02); *A61B 2090/0814* (2016.02); *A61B 2090/308* (2016.02)

(58) Field of Classification Search
CPC . A61B 46/10; A61B 46/00; A61B 2090/0814; A61B 2090/308
USPC ......................................................... 128/849
See application file for complete search history.

(56) References Cited

U.S. PATENT DOCUMENTS

| | | | | |
|---|---|---|---|---|
| 4,559,671 A | * | 12/1985 | Andrews | A61B 46/10 118/504 |
| 4,605,124 A | * | 8/1986 | Sandel | F21V 21/403 16/421 |
| 4,844,252 A | * | 7/1989 | Barron | F21V 21/403 206/223 |

(Continued)

FOREIGN PATENT DOCUMENTS

| | | |
|---|---|---|
| CN | 302490768 S | 7/2013 |
| CN | 302499090 S | 7/2013 |

(Continued)

*Primary Examiner* — Ellen C Hammond
*Assistant Examiner* — David C Comstock
(74) *Attorney, Agent, or Firm* — McGlew and Tuttle, P.C.

(57) ABSTRACT

A protective device (10, 10') provides a protective cover for a part (12, 12', 12") of a medical device and includes a flexible part (14, 14') and with a rigid part (16, 16'). The rigid part (16, 16') has at least one locking element (28, 28'). The locking element (28, 28') is lockingly connectable to a counterpiece of the corresponding part (12, 12', 12") of the medical device.

20 Claims, 12 Drawing Sheets

(56) References Cited

U.S. PATENT DOCUMENTS

| | | | |
|---|---|---|---|
| 4,974,288 A * | 12/1990 | Reasner | A61B 90/36 16/421 |
| 4,976,299 A * | 12/1990 | Bickelman | A61B 46/10 150/155 |
| 5,036,446 A | 7/1991 | Quintanilla et al. | |
| 5,065,296 A * | 11/1991 | Cude | A61B 46/10 362/399 |
| 5,156,456 A | 10/1992 | Hoftman et al. | |
| 5,355,292 A | 10/1994 | Hoftman et al. | |
| 5,408,400 A | 4/1995 | Gordon | |
| 5,465,461 A | 11/1995 | Sandel | |
| 5,700,085 A | 12/1997 | Calderwood | |
| 5,709,465 A | 1/1998 | Lanzone | |
| 5,735,598 A | 4/1998 | Ramirez | |
| 5,884,996 A * | 3/1999 | Cottone | A61B 46/10 362/399 |
| 6,447,149 B1 | 9/2002 | Kaforey et al. | |
| 8,752,987 B1 * | 6/2014 | Hoftman | A61B 46/10 362/400 |
| 2002/0088089 A1 | 7/2002 | Horan et al. | |
| 2002/0089857 A1 | 7/2002 | Borders et al. | |
| 2003/0014834 A1 * | 1/2003 | Naughton | A61B 90/36 16/110.1 |
| 2003/0161158 A1 | 8/2003 | Jesurun et al. | |
| 2003/0210559 A1 | 11/2003 | Jesurun et al. | |
| 2009/0133226 A1 | 5/2009 | Halamish et al. | |
| 2014/0071701 A1 | 3/2014 | Lawrence et al. | |
| 2014/0075721 A1 | 3/2014 | Denmark | |
| 2017/0056120 A1 * | 3/2017 | Benatav | A61B 46/10 |

FOREIGN PATENT DOCUMENTS

| | | |
|---|---|---|
| CN | 104590787 A | 5/2015 |
| CN | 204618410 U | 9/2015 |
| CN | 303442284 S | 11/2015 |
| CN | 105581766 A | 5/2016 |
| DE | 10 2008 061 362 A1 | 6/2010 |
| EP | 3 056 164 A1 | 8/2016 |
| WO | 89/07900 A1 | 9/1989 |
| WO | 90/02292 A1 | 3/1990 |
| WO | 2015/158397 A1 | 10/2015 |

* cited by examiner

PROTECTIVE COVER FOR A PART OF A MEDICAL DEVICE

CROSS REFERENCE TO RELATED APPLICATIONS

This application is a United States National Phase Application of International Application PCT/EP2017/001296 filed Nov. 8, 2017, and claims the benefit of priority under 35 U.S.C. § 119 of German Application 10 2016 013 394.5, filed Nov. 11, 2016, the entire contents of which are incorporated herein by reference.

TECHNICAL FIELD

The present invention pertains to a device (protective device) acting as a protective cover for a part of a medical device, especially for a handle of a medical device, for example, to a lamp (operating lamp) intended for use in an operating room.

TECHNICAL BACKGROUND

Medical devices and hence also medical devices intended for use in an operating room must frequently be set or adjusted manually by the medical staff during use, for example, during a surgery. Such medical devices have handles or the like for this purpose, which must be sterile in order to prevent transmitted infections by a user to a patient or vice versa. Such handles are usually replaced, for example, before each surgery for this purpose, or a protective device in the form of a sterile cover intended for disposable use or in the form of a disposable cover is arranged on the handle.

Such disposable covers usually consist of a bag made of a plastic, which is pushed over the handle in question. The bag is kept open by a stable part at the open end. The protective device is often connected to the handle in a non-positive or positive-locking manner by means of the stable part. In addition or as an alternative, a vacuum generated while a protective device is being arranged on the handle in question is also used for holding on the handle due to the inflow of air into the interior of the protective device being prevented by good sealing.

Depending on the configuration, the manufacture of prior-art protective devices is expensive, especially because the individual components, especially individual components in the form of, for example, deep-drawn plastic parts, are already expensive and multipart protective devices must be connected to one another by means of complicated processes.

The arrangement of prior-art protective devices on a medical device is at times very difficult precisely in case of non-positive connections to the handle in question, because arrangement with only one hand is very complicated and another person must therefore sometimes hold up nonsterile components of the medical device.

Furthermore, it cannot readily be recognized after a use of prior-art protective devices whether the product in question was already mounted. Therefore, disposable products imply the latent risk of infecting patients and users due to negligent or willful multiple use.

Finally, prior-art protective devices in a particular packaging have a relatively large volume. This leads to an increase in the cost of sterilization, in the cost of sterile packaging and in the space needed for storage, the latter being especially critical in case of storage in the operating room or in a surgical department because the space available there is incomparably more limited.

SUMMARY

Based on the observations outlined above concerning prior-art protective devices, one object of the present invention is to provide a protective device for a handle of a medical device, which is characterized by improvements in respect to individual drawbacks mentioned above or in respect to a plurality of the aforementioned drawbacks.

This object is accomplished according to the present invention by a protective device for a handle of a medical device, which device comprises a first, flexible part and a second, firm part (a harder part or essentially rigid part—hereinafter rigid part), for the flexible part to cover at least a grip area of the handle entirely when the protective device is arranged on the handle. The rigid part is configured to mesh detachably with a base area of the handle. The rigid part comprises at least one locking element for the detachable fixation at the base area.

The protective device being provided for a handle of a medical device accordingly comprises a rigid part intended for the fixation of the protective device on the handle as well as a flexible, bag-type part intended for covering at least the grip area of the handle, wherein the two parts are connected to one another and wherein the rigid part has at least one locking element, which can be detachably connected, for example, lockingly detachably connected, to a counterpiece of the handle. Typical medical devices, on the handles of which such a protective device can advantageously be used, are, for example, operating lamps and monitor mounts.

One advantage of the present invention is that the protective device can be arranged on the handle in question and fixed thereto easily, especially with only one hand, without the need to touch in the process the area surrounding the handle and the medical device itself and hence nonsterile parts. In addition, the division into a flexible part and a rigid part leads to an advantageously small package size, the needed volume being determined essentially by the rigid part.

In one embodiment of the protective device, the latter has in its rigid part a thread or section intended for interacting with a thread or with a section in the base area of the handle in question. An especially reliable fixation of the protective device at the handle in question is guaranteed by means of such a thread or section.

In one embodiment of the protective device, the latter has turning assistance on its rigid part. Such turning assistance facilitates the rotary motion of the rigid part relative to the base area of the handle, which are necessary for fixing the protective device on the handle in question.

The fixation of the protective device on the handle in question can be eliminated especially easily and in an especially uncomplicated manner if the protective device has at the rigid part an unlocking device for releasing the locking element from a fixation in the base area of the handle.

In a special embodiment of the protective device, the latter has at the rigid part at least one predetermined breaking point associated in space with the unlocking device. When the unlocking device is actuated, for example, during a pull exerted by the hand of the user on the unlocking device, the predetermined breaking point or at least one predetermined breaking point will yield, so that an irreversible deformation of the rigid part of the protective device will result. Based on such a deformation, it can reliably be recognized at any time whether the protective device was already in use. An unintended multiple use of the protective device can thus effectively be prevented.

A special embodiment of the protective device is characterized by a rigid, plate-shaped rigid part. The rigid part is adapted with the plate shape especially well to the usual shape of a base area of a handle on a medical device. Moreover, the plate-shaped rigid part can be arranged especially well at the base part and the protective device as a whole can thus be arranged especially well at the handle. Such a rigid part will hereinafter accordingly also be called mounting plate. The plate shape, i.e., the round shape, of the rigid part guarantees, in addition, good guiding of the flexible part of by the rigid part on all sides, so that the flexible part is properly in contact with the grip area of the handle when the protective device is arranged at a handle.

In an alternative embodiment of the protective device, the latter comprises a clamp as a rigid part, which is connected to the flexible part at least in partial areas. Such a clamp is elastically movable within the framework of its material properties and makes it possible on compression, for example, to open the flexible part connected to the clamp. This facilitates the arrangement of the protective device on a particular handle, namely, the pulling of the flexible part over the grip area of the handle. In addition, the clamp is a flat component and the protective device will correspondingly have an advantageously small package size in the unused state, the clamp essentially determining the needed area of the package.

In one embodiment of a protective device with a clamp as a rigid part, this protective device has at least one locking hook, which acts as a locking element and which meshes with a locking area of the handle during the fixation at the handle, for the detachable fixation of the protective device at a particular handle at the clamp.

In another special embodiment of a protective device with a clamp as a rigid part, this protective device has two straps, which are articulated at the clamp and are connected to the flexible part in the edge area thereof in at least some sections. These straps open the flexible part during the compression of the clamp in a defined manner and hold, moreover, the flexible part at the edges thereof on all sides, so that the flexible part is properly in contact at least with the grip area of the handle on all sides when the protective device is arranged on a handle.

On the whole, the invention being proposed here is also a system, which comprises a protective device of the type herein and hereinafter described, on the one hand, and a handle of a medical device, on the other hand, wherein the handle has a grip area and a base area. In a special embodiment of such a system, the base area of the handle is set up for the detachable fixation of the rigid part of the protective device at the handle and has for this purpose at least one locking area for receiving the locking element of the protective device. At least one predetermined breaking point is preferably provided, and is configured such that it breaks when the protective device is unlocked, thus clearly showing a past use of the protective device and ruling out a repeated use of the device.

In another embodiment of such a system, the locking area has a joining area, a catching area and a stop area with a guide slope in between. The joining area is intended to receive the locking element of the protective device when the protective device is connected to the handle and receives the locking element during the initial connection of the protective device to the handle. The locking element of the protective device can be deflected by means of the guide slope during the connection of the protective device to the handle and during the rotation of the rigid part relative to the base area of the handle and is deflected when the protective device is connected to the handle and the rigid part is rotated relative to the base area of the handle. During the further rotation of the rigid part, the locking element moves from the guide slope into the catching area and acts there to bring about the locking fixation of the rigid part at the base area of the handle.

Exemplary embodiments of the present invention will be explained in more detail below on the basis of drawings. Objects or elements corresponding to one another are provided with the same reference numbers in all figures.

The exemplary embodiment or each exemplary embodiment shall not be considered to be a limitation of the present invention. Rather, variations and modifications are possible, especially such variants and combinations which the person skilled in the art can find, for example, by a combination or modification of individual features that are described in connection with the general or special part of the specification as well as are contained in the claims and/or in the drawings with a view to accomplishing the object and which lead to a new subject through combinable features. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
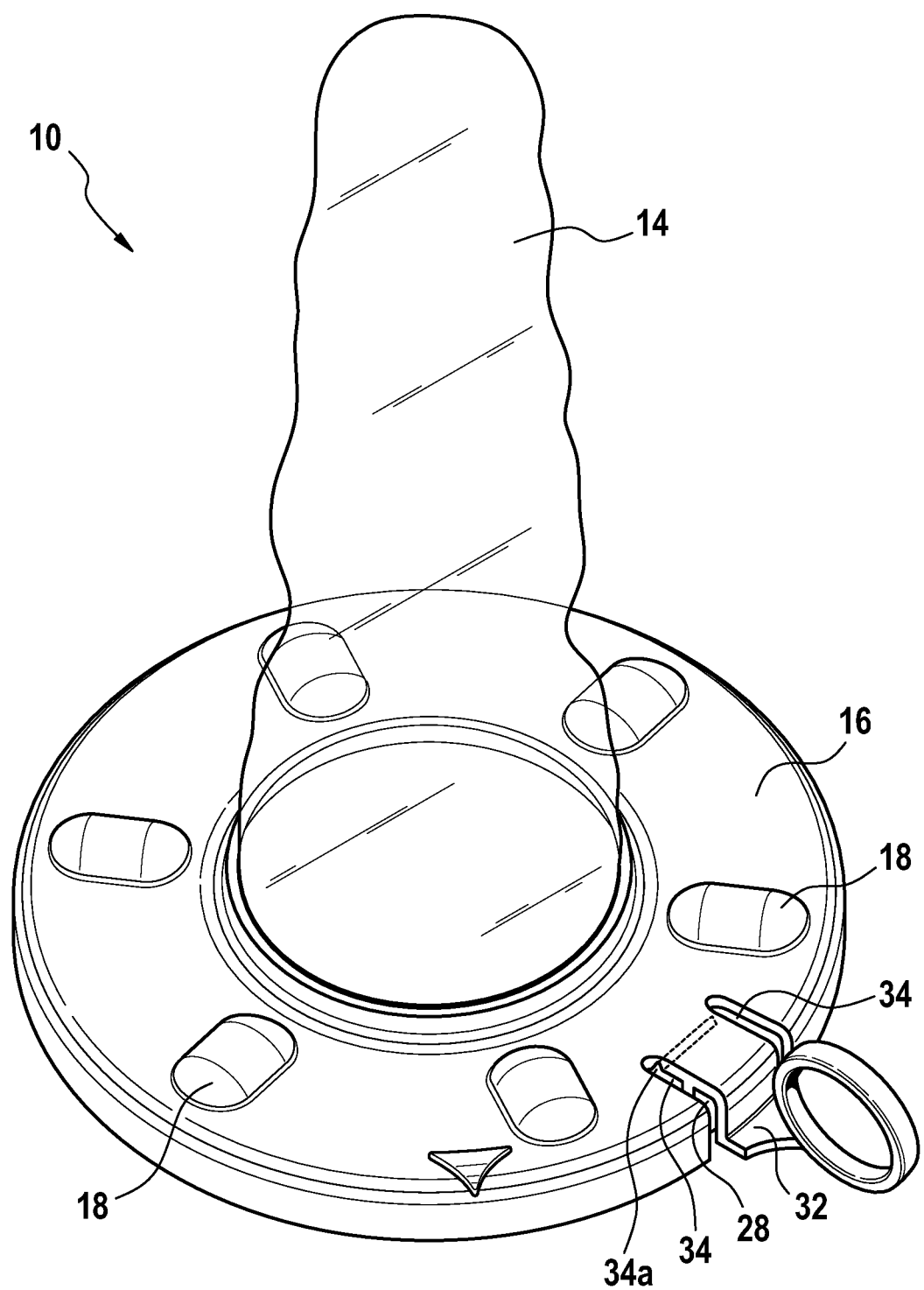
FIG. 1 is a perspective view of a protective device for a handle of a medical device.
Figure 2:
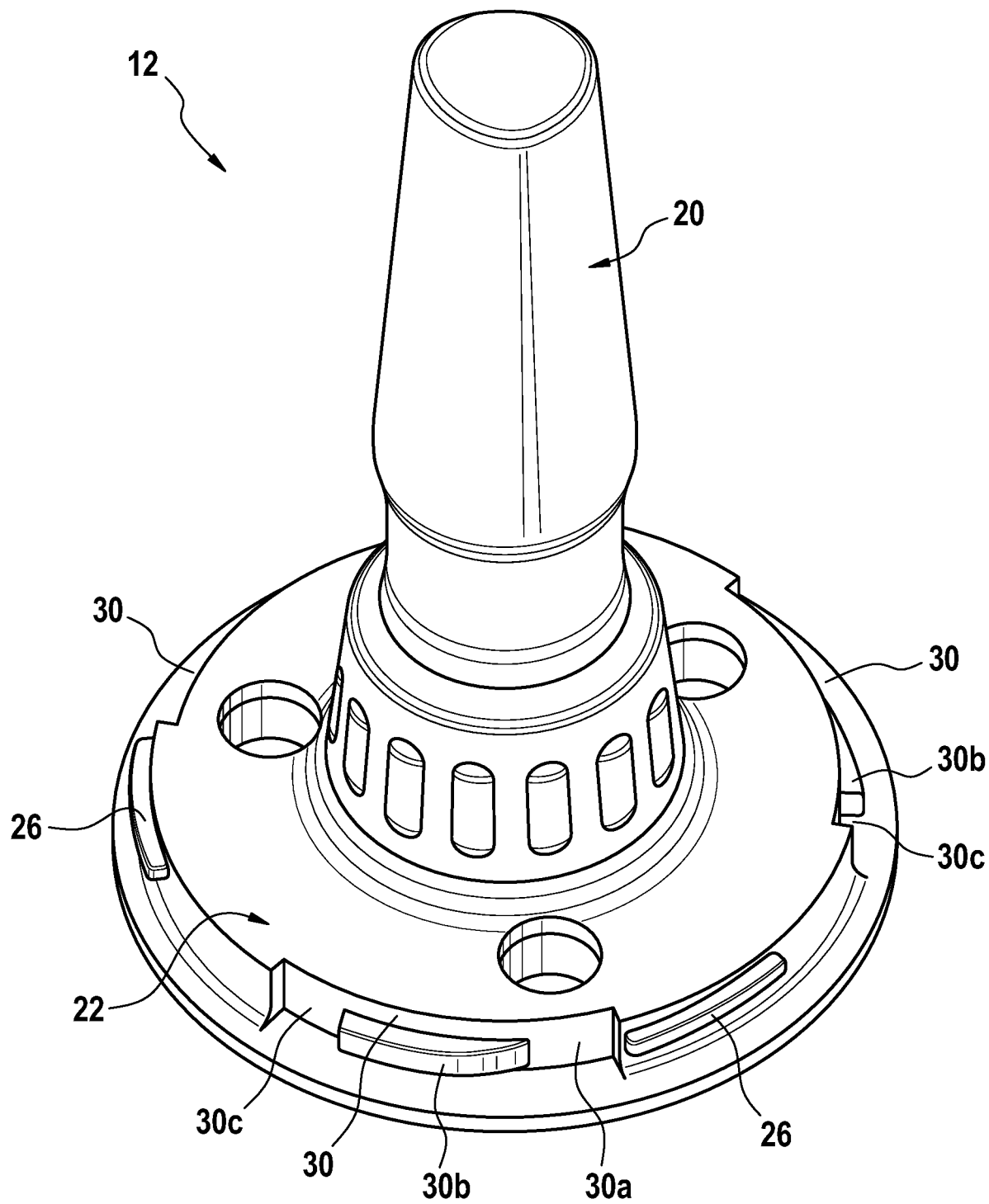
FIG. 2 is a perspective view of a handle intended for arranging a protective device according to FIG. 1.

Referring to the drawings, the view in FIG. 1 shows as an example an embodiment of the protective device 10 proposed here for a handle 12 (FIG. 2) of a medical device, which is not shown itself, for example, of a medical device in the form of an operating lamp or of a monitor mount. The protective device 10 comprises two parts connected to one another, namely, a first, flexible part 14, which is pulled over the handle 12 and will hereinafter be called bag 14, as well as a second, fixed (rigid) part 16, by means of which the protective device 10 is fixed on the handle in question 12 and which will hereinafter be called mounting plate 16.

The mounting plate 16 and the bag 14 preferably consist of a plastic. The bag 14 is permanently connected to the mounting plate 16. The connection may be brought about, for example, by welding, bonding or by means of a suitable additional component by clamping. The handle 12 has a grip area 20 as well as a base area 22. At least the grip area 20 of the handle 12 is entirely covered by means of the bag 14 of the protective device 10 when the protective device 10 is arranged on the handle 12. The protective device 10 removed from a sterile packaging is now connected detachably to the handle 12 by the bag 14 being pulled over the grip area, and the mounting plate 16 is arranged detachably on the base area 22.

At the mounting plate 16, the protective device 10 has optional rotation (gripping) aids 18, in or at which the fingers of a user are supported in order to rotate the mounting plate 16 of the protective device 10 during the arrangement on the medical device in question. The turning assistance 18 may have an elevated and/or recessed configuration relative to the adjacent surface of the mounting plate 16.

Figure 3:
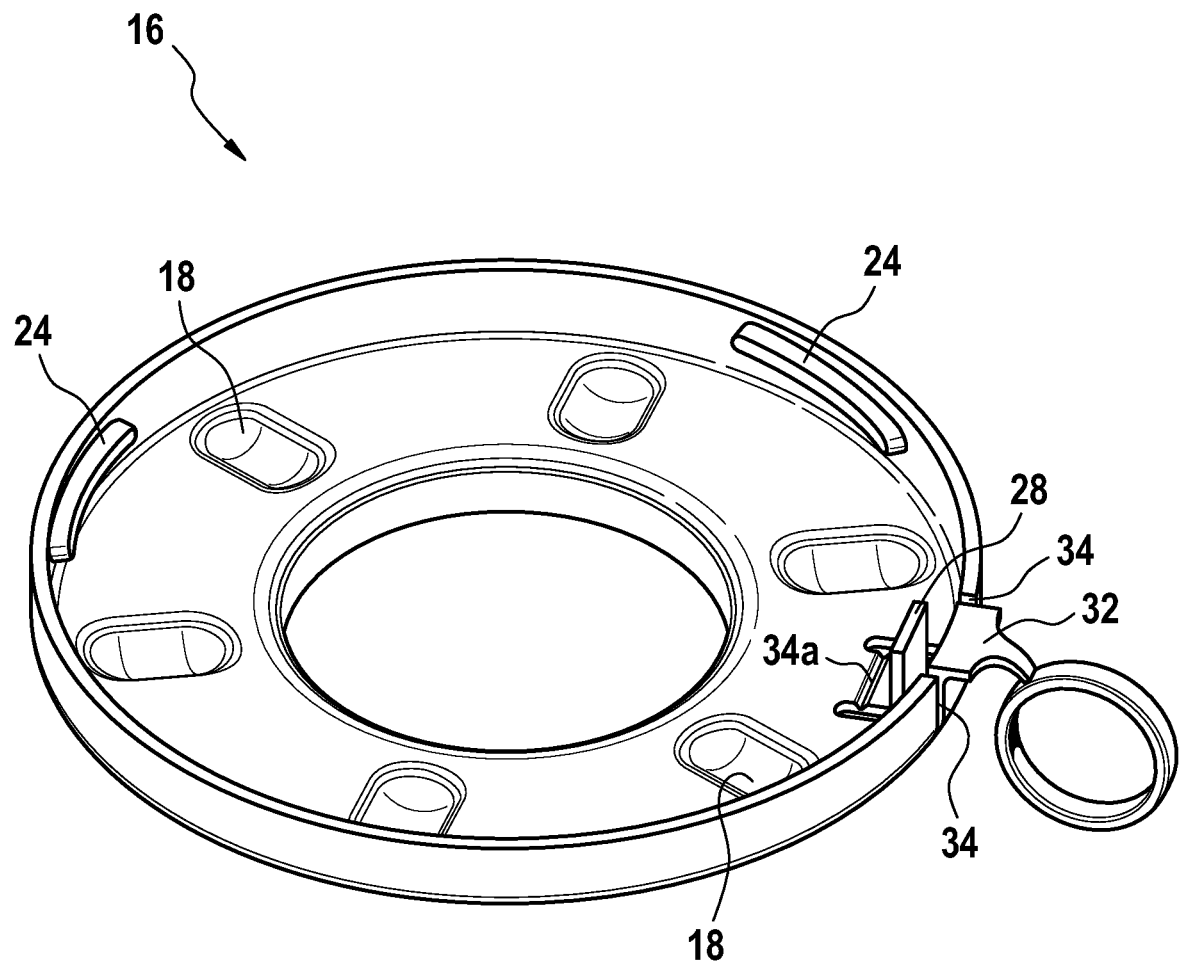
FIG. 3 is a perspective view of a mounting plate of the protective device according to FIG. 1.

The view in FIG. 3 shows the underside of the mounting plate 16. The protective device 10 can be connected to the handle 12 of the particular medical device in a positive-locking manner by means of a section or thread 24, which can be seen here and is enclosed by the mounting plate 16, and it is connected to this in a positive-locking manner during the arrangement on a handle 12. The handle 12 or the medical device has a section or thread 26 (FIG. 2) corresponding to the section or thread 24 of the protective device 10. The thread 24 in the mounting plate 16 and the thread 26 at the base area 22 of the handle 12 do not necessarily have to be threads 24, 26 extending continuously helically circumferentially. Short helical sections fitting one another, as they are configured in the embodiment shown, are, in fact, sufficient for a positive-locking connection. As an alternative, for example, a section in the manner of a bayonet coupling or in the form of a bayonet coupling may be considered for use as a section for a positive-locking connection. In the interest of better readability, the description being presented here will be continued based on the example of a thread 24 (internal thread), especially of an internal thread 24 in the form of a plurality of short helical sections, on the side of the mounting plate 16 and of a fitting thread 26 on the side of the handle 12 or of the medical device. Other positive-locking connection possibilities, especially a connection in the form of or in the manner of a bayonet coupling, shall always be implied and expressly considered to be also covered by the description being presented here.

In an optional embodiment, the mounting plate 16 of the protective device 10 comprises a locking element 28, which is embodied in the form of a locking lug (FIG. 3) in the embodiment shown. The locking element 28, especially the locking lug, is intended to lock the protective device 10 in an end position of the rotary motion on the handle 12 and thus to prevent an unintended removal. The locking element 28 meshes for this purpose, especially in a locking manner, with a locking area 30 (FIG. 2) intended for this purpose in the handle 12, especially with a locking area 30 in the form of a recess in the thread 26 of the handle 12.

The locking area 30 is optionally configured such that the locking element 28 of the mounting plate 16 is moved by means of the locking area 30 into an end position during the rotation of the mounting plate 16 and is locked in this position. In the embodiment shown, the locking area 30 is several times longer for this purpose than the width of the locking lug acting as a locking element 28 along the outer circumferential surface of the base area 22. The locking area 30 is divided concretely into a joining area 30a, a stop area with a guide slope 30b and a catching area 30c.

The joining area 30a and the catching area 30c are slightly broader along the outer circumferential surface of the base area 22 of the handle 12 than the locking lug, being at least so broad that the joining area 30a and the catching area 30c can receive the locking lug (locking element 28).

When arranging the protecting device 10 and when combining the mounting plate 16 thereof with the base area 22 of the handle 12, the mounting plate 16 is or will be oriented first relative to the base area 22 such that the locking lug enters into the joining area 30a of the locking area 30. It is only then that the mounting plate 16 can be placed entirely on the base area 22, so that the thread 24 of the mounting plate 16 will mesh with the thread 26 of the base area 22. The thread 24, 26 becomes increasingly fixed during the subsequent rotation of the mounting plate 16 relative to the base area 22 of the handle 12, and the locking lug enters at the same time the stop area and slides along the guide slope 30b, while the free end of the locking lug is deflected radially outwards due to the elasticity of its material (pushed outwards along with a reversible deformation). During continued further rotation of the mounting plate 16 on the base area 22, the locking lug finally enters the catching area 30c. The locking lug now leaves the guide slope 30b and is elastically deflected into the catching area 30c without the previous deflection based on the guide slope 30b. The catching area 30c is defined by the end of the locking area 30 in the direction of the previous rotation and by the end of the guide slope 30b in the opposite direction. This end of the guide slope 30b is not beveled, so that the locking lug snapped into the catching area 30c prevents a further rotation of the mounting plate 16, but also a backward rotation of the mounting plate 16. The mounting plate 16 is thus fixed in an end position defined by the locking area 30 at the handle 12, namely at the base area 22 thereof, as a result of which the protective device 10 as a whole is fixed at the handle 12.

The locking area 30 is optionally present on the circumference of the base area 22 as a plurality of locking areas, especially in a manner interrupting the thread 24. In the embodiment shown, the base area 22 of the handle 12 has a plurality of equidistant locking areas 30, namely, three locking areas 30, and three areas with one corresponding section each of the thread 26 alternate with the three locking areas 30 along the outer circumference of the base area 22.

In a special variant of this embodiment, the locking element 28 is used as a fixed stop in order to define an unambiguous end position of the mounting plate 16 relative to the base area 22 during the arrangement of the protective device 10 on the handle 12, which takes place by the mounting plate 16 being "screwed" onto the base area 22.

For unlocking a protective device 10 fixed on a handle 12, an unlocking device 32, which may have, for example, a grip ring at the end thereof for easier handling, is provided at the protective device 10. The locking element 28 is disengaged from the locking area 30 by means of the unlocking device 32. Without actuating the locking element 28, which is fixed in, especially snapped into, the locking area 30, the mounting plate 16 cannot be detached from the handle 12 even by means of a rotary motion, and the protective device 10 as a whole cannot thus be removed from the handle 12.

In a special embodiment, an area around the unlocking device 32 is irreversibly deformed, for example torn off, during the unlocking. This is supported by a suitable configuration of the mounting plate 16 in this area, for example, in the form of at least one predetermined breaking point 34a in his area, especially of a predetermined breaking point 34 in the form of a notch or another weakening of the material. In the embodiment shown, the predetermined breaking point 34a adjoins at least one slot 34 in the mounting plate 16, namely, a slot 34 or two parallel or essentially parallel slots 34, which slot or slots makes/make possible a mobility of the locking device 32. When the predetermined breaking point 34a is broken, the mounting plate 16 is irreversibly deformed after the unlocking by means of the unlocking device 32. The user can thus recognize the protective device 10 as "already used." Reuse of the protective device 10 intended to be a disposable product is thus effectively prevented.

Figure 4:
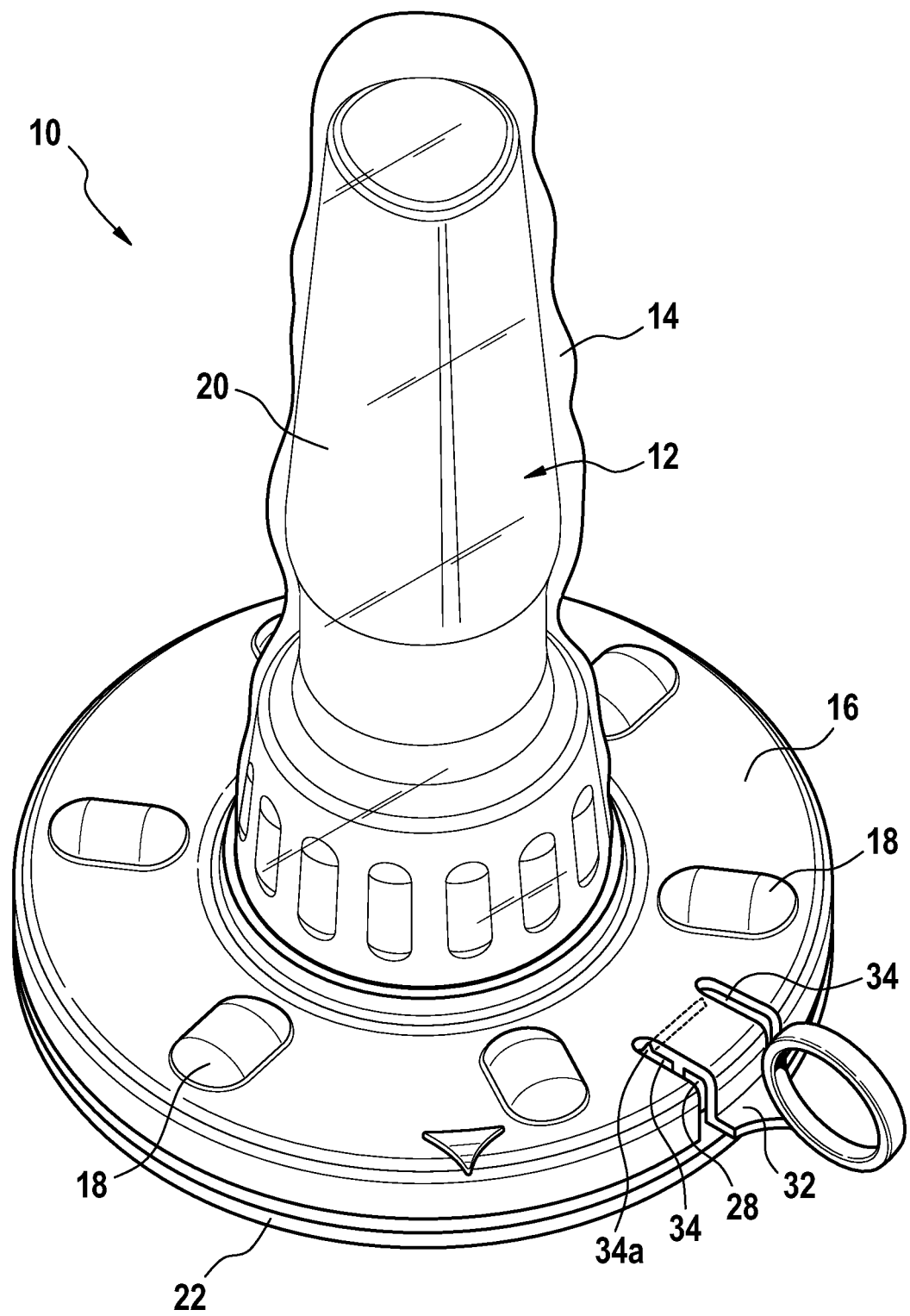
FIG. 4 is a perspective view of a protective device according to FIG. 1, which is arranged on a handle.

The view in FIG. 4 shows a protective device 10 according to FIG. 1, which is arranged on a handle 12. The bag 14 of the protective device 10 fully encloses the grip area 20 of the handle 12 and thus seals this entirely. The mounting plate 16 of the protective device 10 is arranged at the base area 22 of the handle 12 by its thread 24 meshing with the thread 26 on the base area 22. In case of a protective device 10 with a locking element 28 and with an unlocking device 32, the locking element 28 is fixed in the or in a locking area 30 of the base area 22 when the protective device 10 is arranged at the handle 12 as intended, and it can be detached from this fixation by means of the unlocking device 32.

Figure 5:
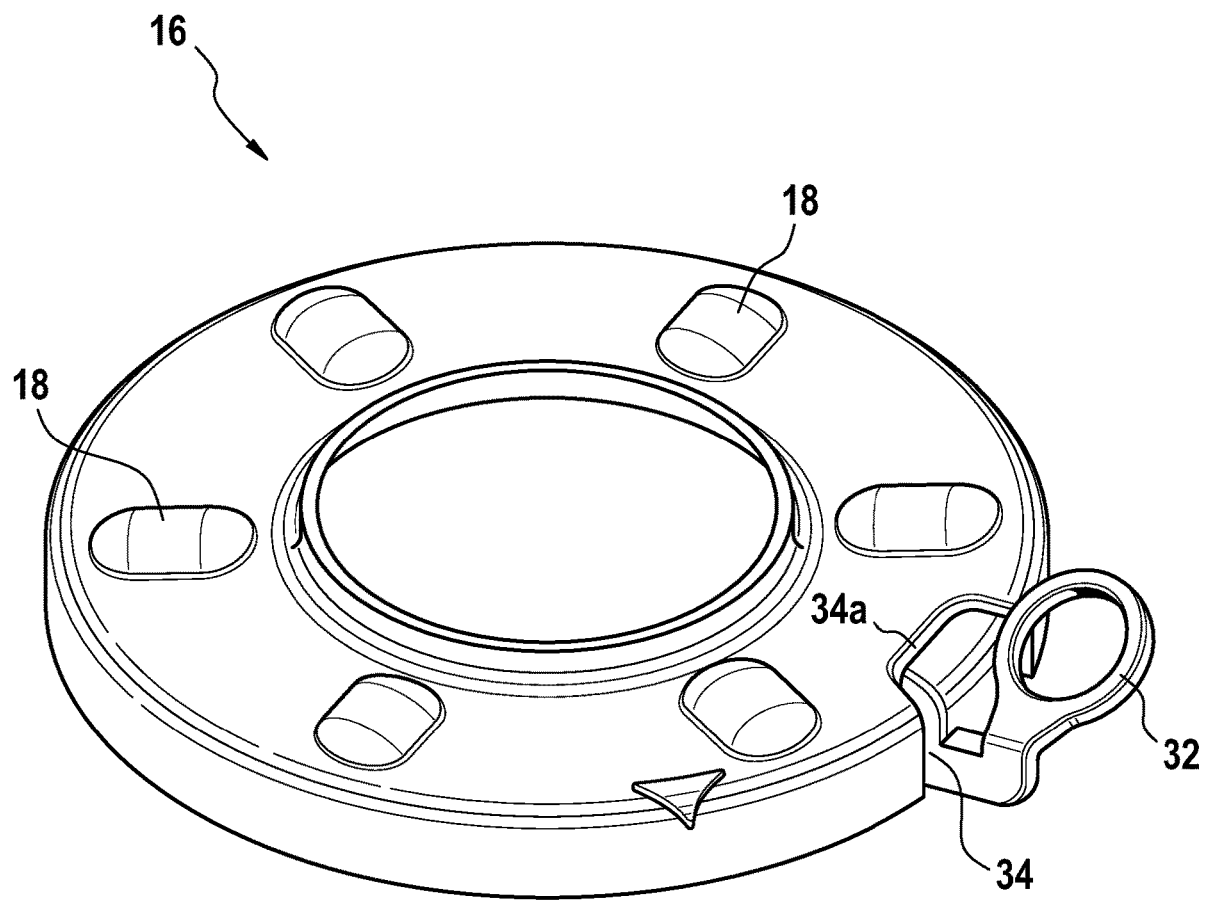
FIG. 5 is a perspective view of an alternative embodiment of a mounting plate for a protective device according to FIG. 1.

The view in FIG. 5 shows a special embodiment of the mounting plate 16, wherein the bag 14 (FIG. 1) arranged on the mounting plate 16 in case of a complete protective device 10 is not shown. The peculiar feature of this embodiment is that the unlocking device 32 is oriented in the direction of the rotary motion of the mounting plate 16 during the removal of the protective device 10 from the handle 12. The mounting plate 16 is thus already rotated in the direction necessary for the removal of the protective device 10 after the unlocking by means of the unlocking device 32.

The views in FIG. 6 through FIG. 12 show another embodiment of a protective device 10' of the type being shown here for a handle 12' (FIG. 7) of a medical device, for example, a medical device in the form of an operating lamp or of a monitor mount, which is likewise not shown here itself. This protective device 10' also has a flexible part 14', hereinafter called a bag 14', as well as a rigid part 16', which is configured as a clamp 16' in this embodiment. The clamp 16' is manufactured, for example, from a metal or a plastic and has at any rate a spring-elastic configuration or a spring-elastic configuration in at least some sections. The bag 14' is permanently connected, for example, welded, bonded or clamped, to the clamp 16' at least in partial areas 40'.

Figure 6:
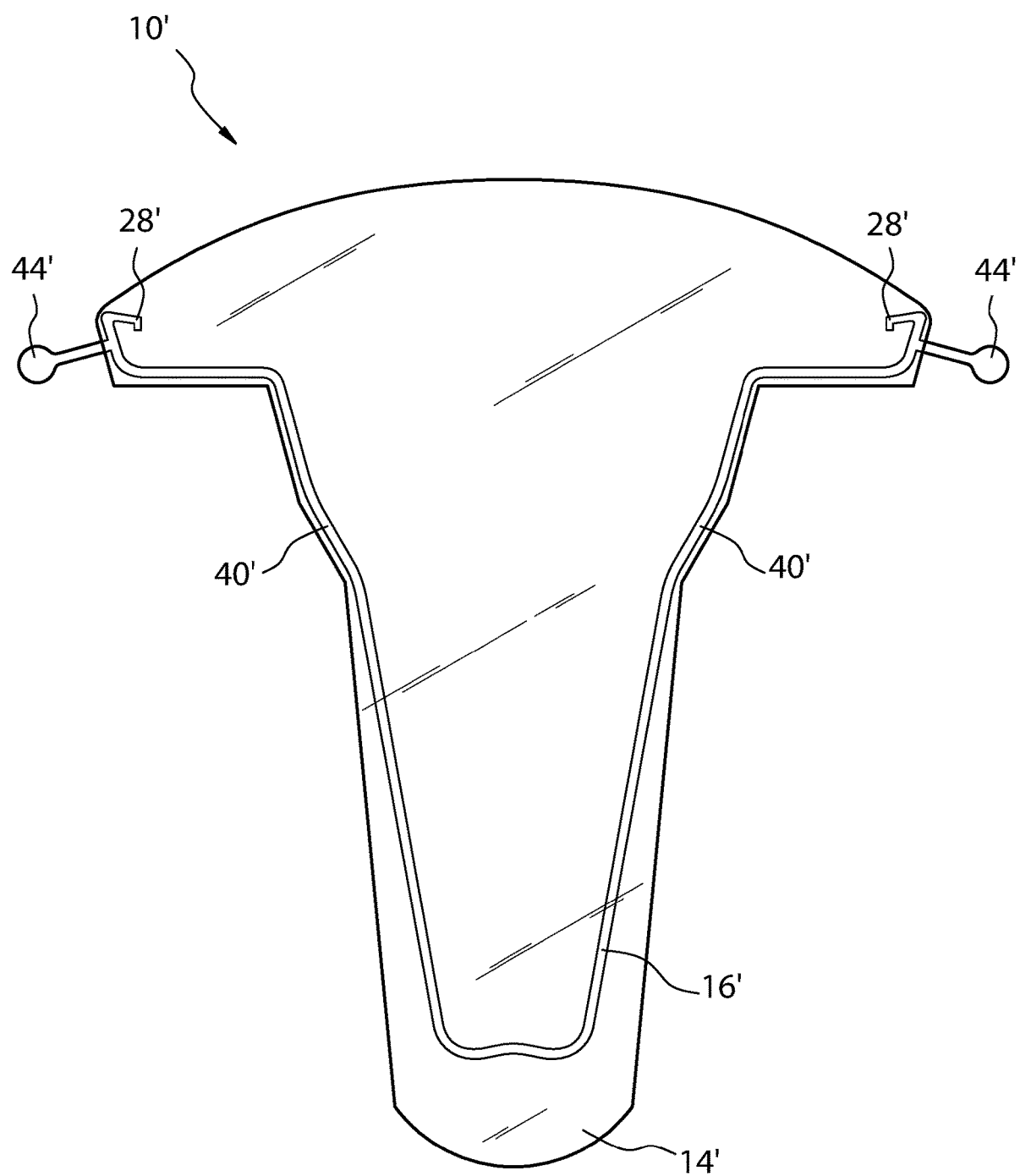
FIG. 6 is a side view of another protective device for a handle of a medical device.
Figure 7:
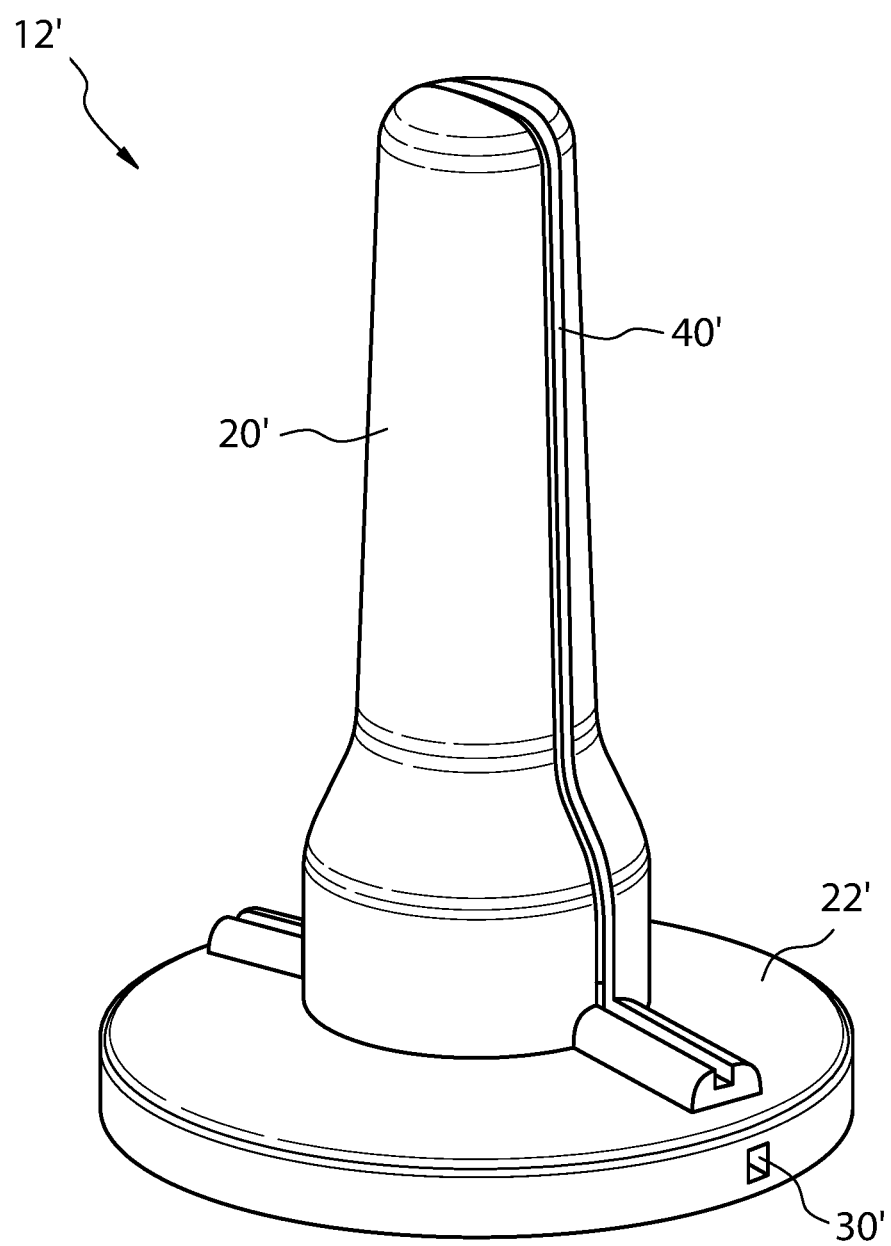
FIG. 7 is a perspective view of a handle intended for arranging a protective device according to FIG. 6.

The protective device 10' according to FIG. 6 is intended for use with a handle 12' according to FIG. 7. This handle has a guide 42' for the protective device 10'. The guide 42' begins in the grip area 20' of the handle 12', especially at the free, upper end of the grip area 20', and reaches the base area 22' of the handle 12'. To arrange the protective device 10' on such a handle 12', the user removes the protective device 10' from a corresponding sterile packaging, and the bag 14' opens by slightly compressing the clamp 16'. The protective device 10' can thus be pushed over the handle 12', while the bag 14' is pushed up optionally farther by the grip area 20' of the handle 12'. With the protective device 10' arranged on the handle 12' as intended, the bag 14' encloses the grip area 20' entirely and thus it covers same completely. The clamp 16' is now guided by means of the guide 42' of the handle 12' and the bag 14' pushes the clamp 16' into the guide 42' due to the internal stress. The guide 42' has, for example, a round, V-shaped or angular profile. As an alternative, guiding of the clamp 16' may also be guaranteed by means of a groove in the clamp 16' and a corresponding spring as a guide 42' at the handle 12' or a spring in the clamp 16' and a corresponding groove as a guide 42' on the handle 12'.

The clamp 16' locks itself in the end position with the base area 22' of the handle 12' by means of a locking element 28' enclosed by the clamp 16'. In the embodiment according to FIG. 6, two locking hooks, which mesh with a corresponding locking area 30' each at the foot of the handle 12', especially in the base area 22' thereof, act as a locking element. To remove the protective device 10' from a handle 12' after the end of use, the locking hooks are unmeshed from the locking area 30' by means of lateral auxiliary grips 44' and the protective device 10' can be pulled off from the grip 12'.

Figure 8:
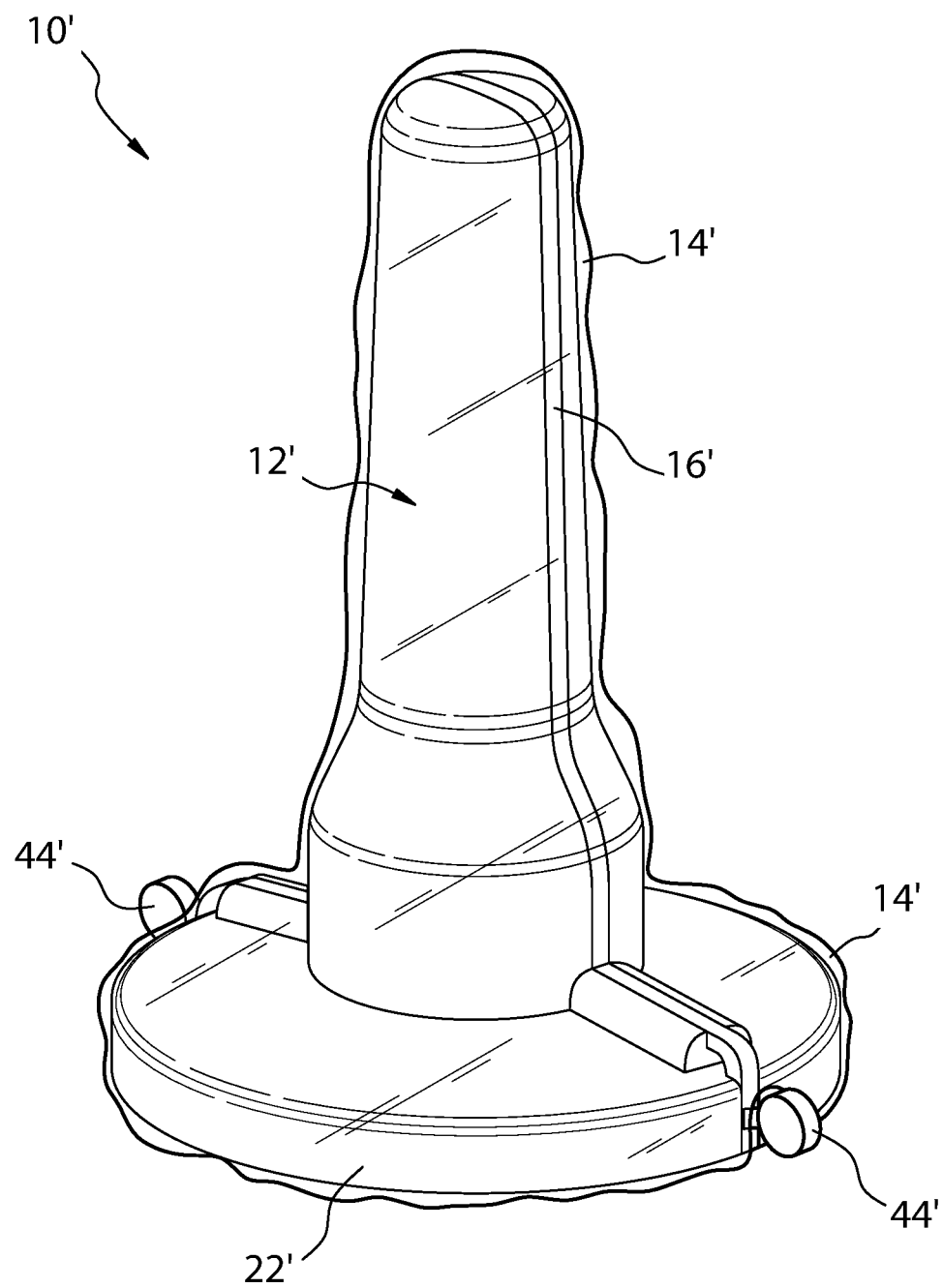
FIG. 8 is a perspective view of a protective device according to FIG. 6, which is arranged on a handle.

The view in FIG. 8 shows a protective device 10' according to FIG. 6, which is arranged on a handle 12' according to FIG. 7. The clamp 16' in the guide 42' at the handle 12' as well as the auxiliary grips 44' for releasing the locking of the clamp 16' at the handle 12' are seen in the interior of the bag 14'.

Figure 9:
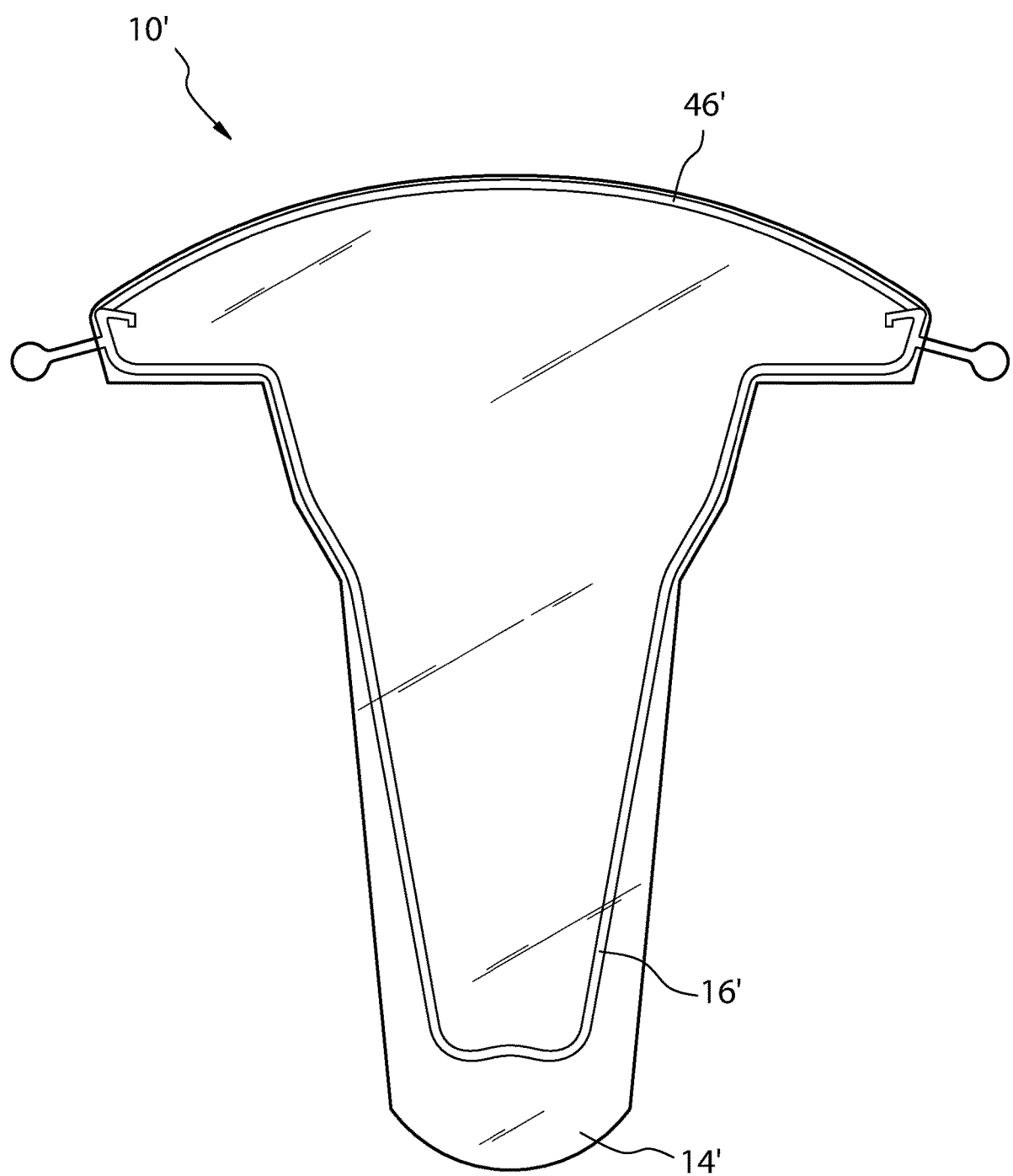
FIG. 9 is a side view of a special embodiment of the protective device according to claim 6.
Figure 10:
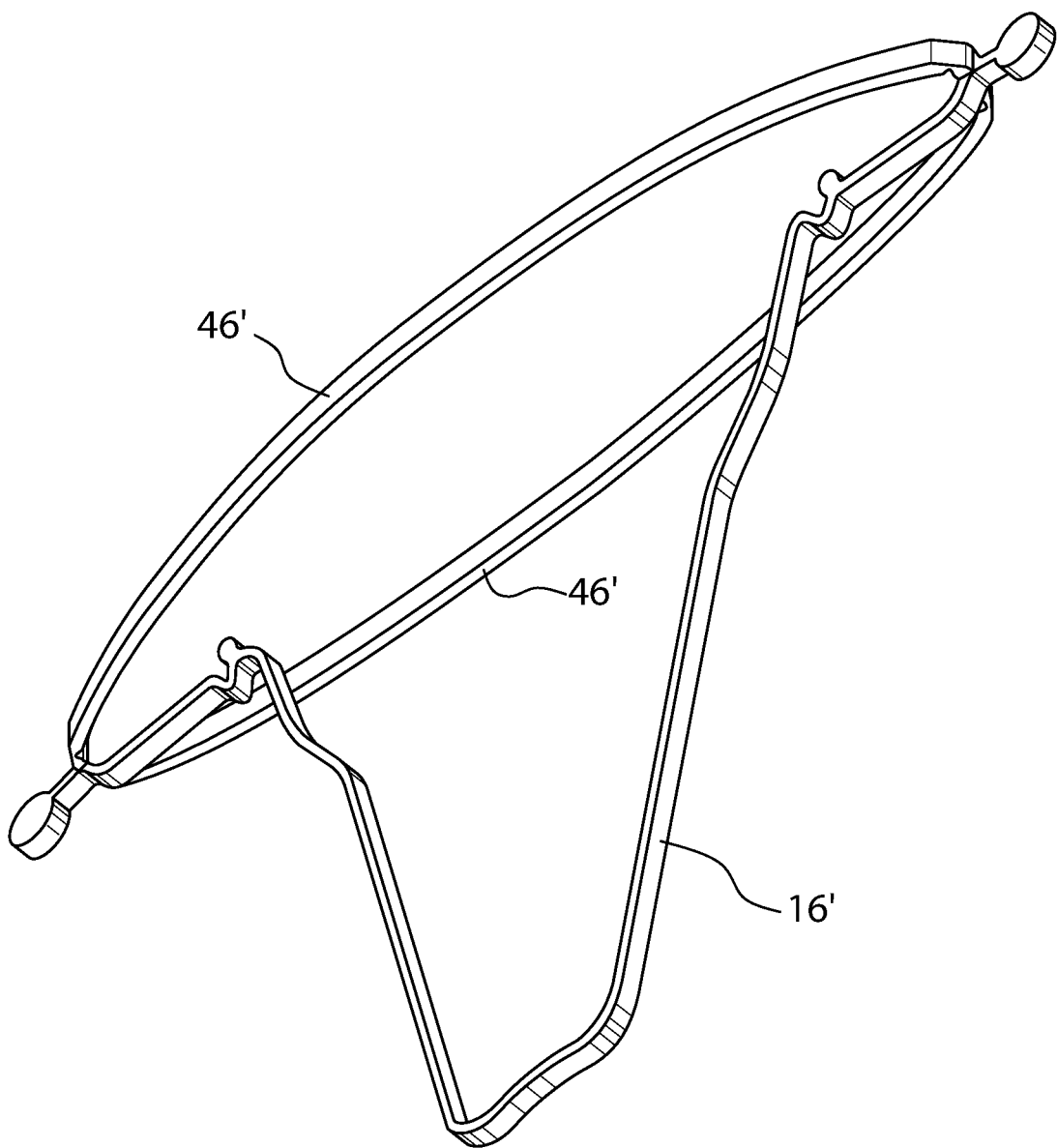
FIG. 10 is a perspective view of a part of the protective device according to FIG. 9.

The views in FIG. 9 and FIG. 10 show a special embodiment of the protective device 10' according to FIG. 6. Two straps 46', only one of which can be seen in the view of the collapsed protective device 10' in FIG. 9, are located here at the free ends of the clamp 16'. It also becomes clear hereby that the straps 46' lie flat when the protective device 10' is in a package (sterile packaging) and become erect only when the protective device 10' is arranged on a handle 12'.

The bag 14' of such a protective device 10' is connected by its edge on the open side to a particular strap 46' each in at least some areas, for example, by welding or bonding. Each strap 46' is arc-shaped already in the relaxed state, and the arc shape predefines a preferential direction during the subsequent deformation when the protective device 10' is arranged on a handle 12'. When the protective device 10' is arranged on a handle 12', the bag 14' is opened, as in the embodiment according to FIG. 6, by compressing the legs of the clamp 16'. The force applied to the ends of the two straps 46' during the compression of the legs of the clamp 16' brings about a deformation of the straps, so that the straps 46' undergo a deformation in the direction of an arc shape with an increasingly smaller radius. In the mounted state on the handle 12', the two straps 46' form a circular shape or approximately a circular shape or at least a shape that corresponds to the shape of the base of the base area 22' of the handle 12'. The straps 46' fix the edges of the bag 14' at the base area 22' of the handle 12', so that as complete a coverage of the handle 12' as possible, and at least full coverage of the grip area 20' thereof, is guaranteed.

The mobility of the straps 46' comprises a folding over from the plane of the clamp 16' (FIG. 9) into a plane extending at right angles or essentially at right angles to the plane of the clamp 16' (FIG. 10) as well as an elastic flexibility. The mobility for folding over from the packaged position into the plane extending at right angles or at least essentially at right angles to the plane of the clamp 16' is guaranteed by means of suitable hinges, for example, film hinges, at the points at which the straps 46' are connected to the clamp 16'. The flexibility of the straps 46' is guaranteed by means of selecting a suitable material. The straps 46' are manufactured, for example, from a plastic.

Figure 11:
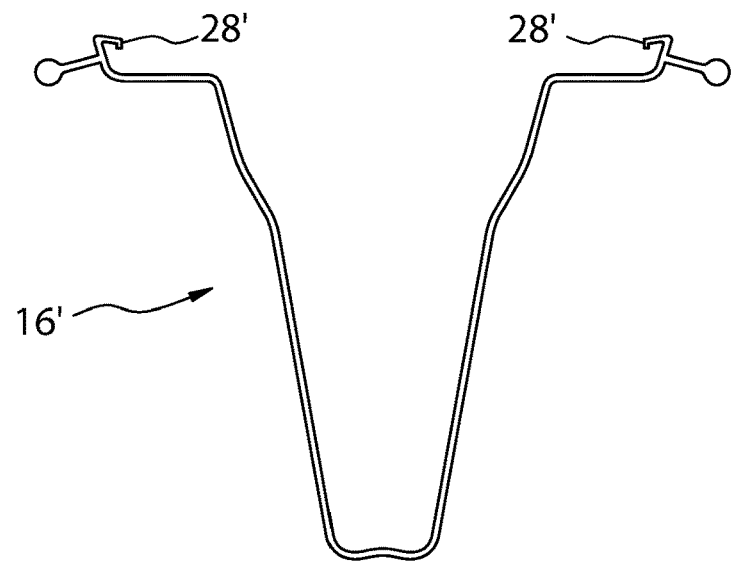
FIG. 11 is a side view of special embodiments of a part of the protective device according to FIG. 6 or FIG. 9.
Figure 11:
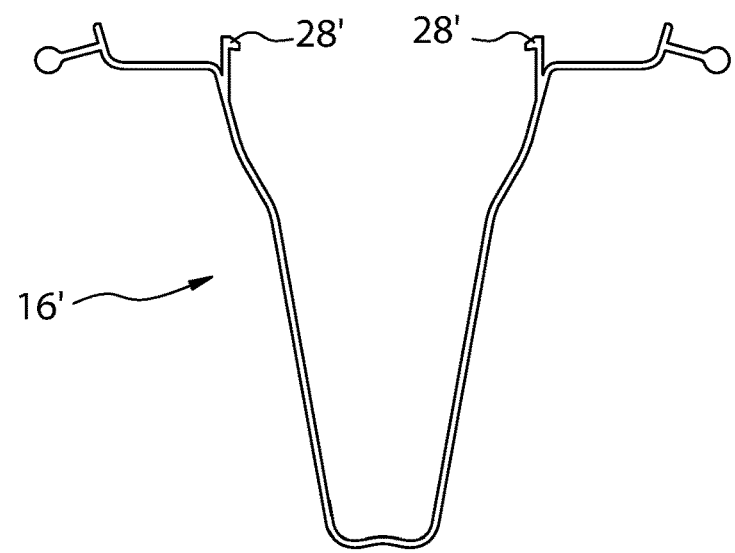
Figure 11:
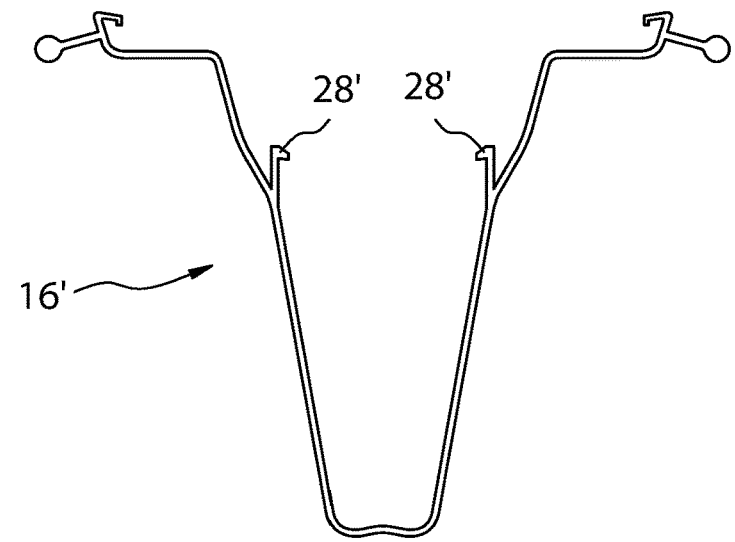

The view in FIG. 11 shows different positions for locking elements 28 arranged in respective pairs at a clamp 16' of the protective device 10'. The handle 12' has corresponding locking areas 30', depending on the variant of the clamp. The locking elements 28' shown in FIG. 11 may also be combined individually or in pairs with additional locking elements 28', for example, such that a clamp 16' has all the locking elements 28' shown in FIG. 11 or some of the locking elements 28' shown in FIG. 11.

Figure 12:
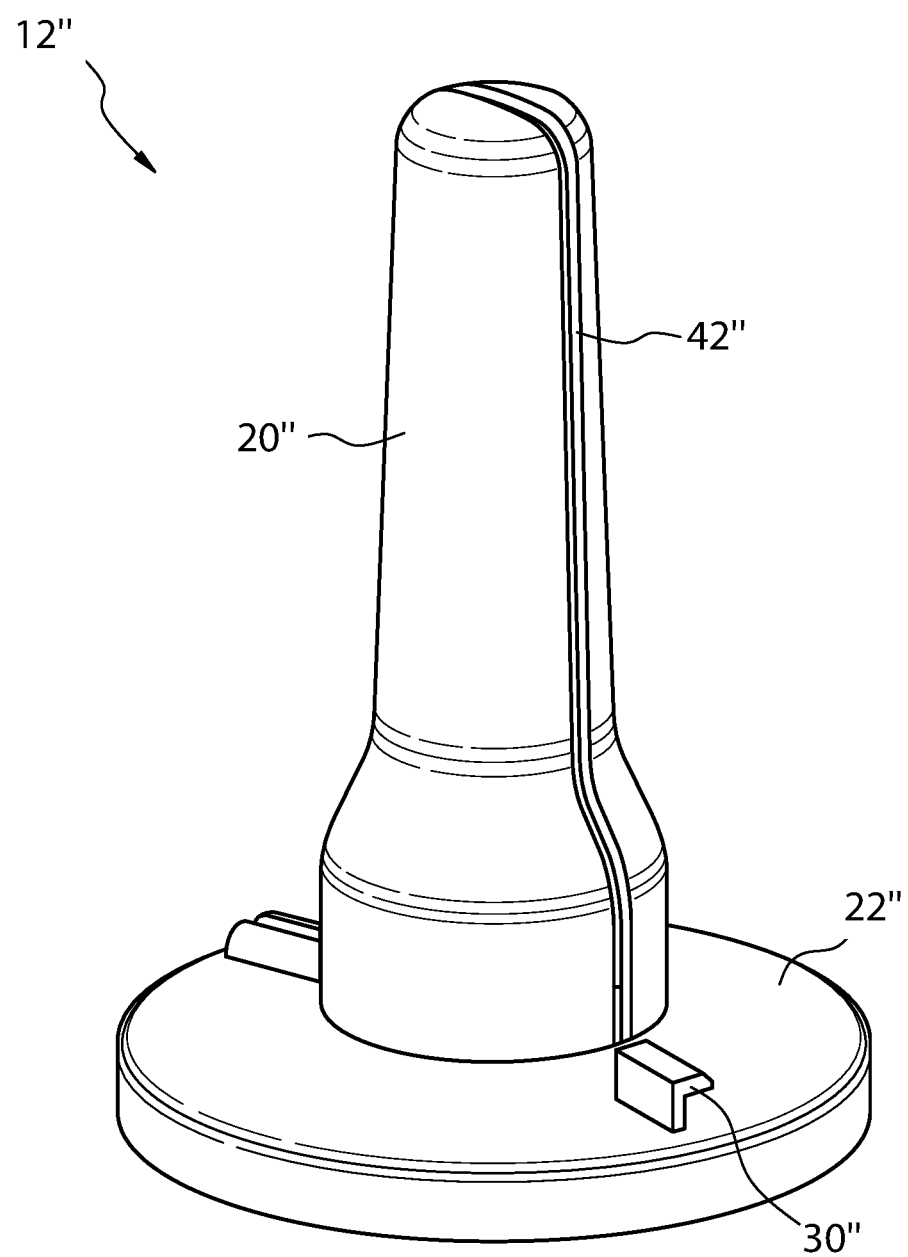
FIG. 12 is a perspective view of an alternative embodiment of a handle intended for arranging a protective device according to FIG. 6.

The view in FIG. 12 finally shows a variant of the handle 12", in which the locking area 30" is configured in the form of a hook at the handle 12", for example, in the form of a hook at the base area 22" of the handle 12". The protective device 10" is fixed with such a locking area 30" at the handle 12" by the corresponding section of the clamp 16" being hooked into the hook.

Individual aspects of the description being submitted here, which are in the foreground, can thus be briefly summarized as follows: Proposed are a protective device 10, 10' with a flexible part 14, 14' and with a rigid part 16, 16', which protective device acts as a protective cover for a part 12, 12', 12" of a medical device, wherein the rigid part 16, 16' has at least one locking element 28, 28', which can be lockingly connected to a counterpiece of the corresponding part 12, 12', 12" of the medical device, as well as a system, which comprises such a protective device 10, 10' and a handle 12, 12', 12" of a medical device, which said handle is intended and set up for arranging such a protective device 10, 10'.

While specific embodiments of the invention have been shown and described in detail to illustrate the application of the principles of the invention, it will be understood that the invention may be embodied otherwise without departing from such principles.

The invention claimed is:

1. A protective device for a handle of a medical device, the protective device comprising:
   a first, flexible part; and
   a second, rigid part, wherein the flexible part covers at least a grip area of the handle with the protective device arranged on the handle, and wherein the rigid part detachably meshes with a base area of the handle and the rigid part comprises at least one locking element for detachable fixation to the base area, the rigid part further comprising a thread or bayonet coupling which thread or bayonet coupling is configured for interaction with a thread or bayonet coupling in the base area in a positive-locking manner.

2. A protective device in accordance with claim 1, wherein the rigid part further comprises turning assistance.

3. A protective device in accordance with claim 1, wherein the rigid part further comprises an unlocking device at the rigid part, which said unlocking device is configured for detaching the locking element from a fixation in the base area of the handle.

4. A protective device in accordance with claim 3, wherein the rigid part further comprises at least one predetermined breaking point associated in space with the unlocking device at the rigid part.

5. A protective device in accordance with claim 1, wherein the rigid part is configured as a rigid, plate-shaped rigid part.

6. A protective device in accordance with claim 1, wherein the thread or bayonet coupling of the rigid part is directly adjacent to an inner surface of the rigid part, the thread or bayonet coupling of the base area being directly adjacent to an outer surface of the base area.

7. A handle arrangement for a medical device, the handle arrangement comprising:
   a handle comprising a base area and a grip area; and
   a protective device, the protective device comprising:
   a first, flexible part; and
   a second, rigid part, wherein the flexible part covers at least the grip area of the handle with the protective device arranged on the handle, and the rigid part detachably meshes with the base area of the handle and the rigid part comprises at least one locking element for detachable fixation to the base area, the rigid part further comprising a thread or bayonet coupling which thread or bayonet coupling is configured for interaction with a thread or bayonet coupling in the base area in a positive-locking manner.

8. A handle arrangement in accordance with claim 7, wherein the rigid part further comprises rotation gripping aids.

9. A handle arrangement in accordance with claim 7, wherein the rigid part further comprises an unlocking device configured for detaching the locking element from a fixation in the base area of the handle.

10. A handle arrangement in accordance with claim 9, wherein the rigid part further comprises at least one predetermined breaking point associated in space with the unlocking device.

11. A handle arrangement in accordance with claim 7, wherein the rigid part is configured as a rigid, plate-shaped rigid part.

12. A handle arrangement in accordance with claim 7, wherein the thread or bayonet coupling of the rigid part is directly adjacent to an inner surface of the rigid part, the thread or bayonet coupling of the base area being directly adjacent to an outer surface of the base area.

13. A handle arrangement in accordance with claim 12, wherein the rigid part is configured to rotate relative to the base area such that rotation of the rigid part brings the thread or bayonet coupling of the rigid part in contact with the thread or bayonet coupling in the base area to connect the rigid part to the base area.

14. A handle arrangement in accordance with claim 7, wherein the thread or bayonet coupling of the base part comprises a thread or bayonet coupling component, the thread or bayonet coupling component being directly adjacent to another portion of the base part.

15. A system comprising:
   a protective device comprising a flexible part and a rigid part comprising at least one locking element; and
   a handle of a medical device, wherein the handle comprises a grip area and a base area, and wherein the base area comprises a locking area configured for detachable fixation of the rigid part of the protective device at the handle with the locking area receiving the locking element of the protective device, the rigid part further comprising a thread or bayonet coupling which thread or bayonet coupling is configured for interaction with a thread or bayonet coupling in the base area in a positive-locking manner.

16. A system in accordance with claim 15, wherein:
   the locking area has a joining area, a catching area and a stop area between the joining area and the catching area and the stop area comprises a guide slope;
   the joining area first receives the locking element during a connection of the protective device to the handle;

the guide slope deflects the locking element during the connection of the protective device to the handle and during a rotation of the rigid part relative to the base area of the handle; and the locking element reaches the catching area from the guide slope during a further rotation of the rigid part and acts at the catching area to bring about the locking fixation of the rigid part at the base area of the handle.

17. A system in accordance with claim 15, wherein the thread or bayonet coupling of the rigid part is directly adjacent to an inner surface of the rigid part, the thread or bayonet coupling of the base area being directly adjacent to an outer surface of the base area.

18. A system in accordance with claim 17, wherein the rigid part is configured to rotate relative to the base area such that rotation of the rigid part brings the thread or bayonet coupling of the rigid part in contact with the thread or bayonet coupling in the base area to connect the rigid part to the base area.

19. A system in accordance with claim 15, wherein the thread or bayonet coupling of the rigid part is directly adjacent to an inner surface of the rigid part, the thread or bayonet coupling of the base area being directly adjacent to an outer surface of the base area.

20. A system in accordance with claim 19, wherein the thread or bayonet coupling of the base part comprises a thread or bayonet coupling component, the thread or bayonet coupling component extending radially outward from another portion of the base part.

\* \* \* \* \*